United States Patent
Packer et al.

(10) Patent No.: US 6,556,695 B1
(45) Date of Patent: Apr. 29, 2003

(54) METHOD FOR PRODUCING HIGH RESOLUTION REAL-TIME IMAGES, OF STRUCTURE AND FUNCTION DURING MEDICAL PROCEDURES

(75) Inventors: Douglas L. Packer, Rochester, MN (US); Richard A. Robb, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 09/397,546

(22) Filed: Sep. 16, 1999

Related U.S. Application Data
(60) Provisional application No. 60/118,765, filed on Feb. 5, 1999.

(51) Int. Cl.[7] .................................................. G06K 9/00
(52) U.S. Cl. ...................................................... 382/128
(58) Field of Search ................................ 382/128, 130, 382/132, 131, 133, 257, 285; 600/450, 438, 443, 440, 424, 408, 458, 447; 424/9.4; 345/418, 419

(56) References Cited

U.S. PATENT DOCUMENTS

| | | | |
|---|---|---|---|
| 5,228,442 A | 7/1993 | Imran | 128/642 |
| 5,321,416 A | 6/1994 | Bassett et al. | 345/8 |
| 5,345,936 A | 9/1994 | Pomeranz et al. | 128/642 |
| 5,345,940 A | 9/1994 | Seward et al. | 128/662.06 |
| 5,391,199 A | 2/1995 | Ben Haim | 607/122 |
| 5,409,000 A | 4/1995 | Imran | 128/642 |
| 5,435,310 A * | 7/1995 | Sheehan et al. | 128/653.1 |
| 5,443,489 A | 8/1995 | Ben Haim | 607/115 |
| 5,465,717 A | 11/1995 | Imran et al. | 128/642 |
| 5,480,422 A | 1/1996 | Ben Haim | 607/122 |
| 5,507,802 A | 4/1996 | Imran | 607/128 |
| 5,545,120 A | 8/1996 | Chen et al. | |
| 5,546,951 A | 8/1996 | Ben Haim | 128/702 |
| 5,547,445 A | 8/1996 | McKenna et al. | |
| 5,553,611 A | 9/1996 | Budd et al. | 128/642 |

(List continued on next page.)

FOREIGN PATENT DOCUMENTS

| | | |
|---|---|---|
| EP | 0732083 A2 | 9/1996 |
| WO | 99-00052 | 1/1999 |

OTHER PUBLICATIONS

Multidimensional Cardiac Imaging, Acoustical Imaging, vol. 2, Dec. 9, 1992, pp. 403–411, Greenleaf, et al.

Abstract—*Intracardiac Ultrasound Guidance of Multipolar Atrial and Ventricular Mapping Basket Applications*, American College of Cardiology, 46th Annual Scientific Discussion, Douglas L. Packer.

*Multipolar Endocarcial Mapping of the Right Atrium During Cardiac Catheterization Description of a New Technique*, JACC vol. 22, No. 4, Oct. 1993:1105–10, Kathy J. Jenkins, et al.

Primary Examiner—Jayanti K. Patel
Assistant Examiner—Seyed Azarian
(74) Attorney, Agent, or Firm—Quarles & Brady, LLP

(57) ABSTRACT

Images of a heart are acquired with a high resolution medical imaging system used to construct a dynamic high resolution 4D model. During a medical procedure such as endocardial physiology mapping and ablation, real-time images are produced by an ultrasonic transducer inserted into the heart. The high resolution heart model is registered with the acquired real-time images and used to produce dynamic, high resolution images for display during the medical procedure. An electrical activation map which depicts the spatial distribution of heart wall electrical activation is merged with the anatomic images to facilitate cardiac ablation therapy.

39 Claims, 8 Drawing Sheets

U.S. PATENT DOCUMENTS

| | | | |
|---|---|---|---|
| 5,558,073 A | 9/1996 | Pomeranz et al. | 128/642 |
| 5,558,091 A | 9/1996 | Acker et al. | 128/653.1 |
| 5,568,384 A | 10/1996 | Robb et al. | 364/419.13 |
| 5,568,809 A | 10/1996 | Ben Haim | 128/656 |
| 5,578,007 A | 11/1996 | Imran | 604/95 |
| 5,662,108 A | 9/1997 | Budd et al. | 128/642 |
| 5,694,945 A * | 12/1997 | Ben-Haim | 128/736 |
| 5,713,946 A | 2/1998 | Ben-Haim | 607/122 |
| 5,718,241 A | 2/1998 | Ben-Haim et al. | 128/702 |
| 5,729,129 A | 3/1998 | Acker | 324/207.12 |
| 5,737,506 A | 4/1998 | McKenna et al. | |
| 5,738,096 A | 4/1998 | Ben-Haim | 128/653.1 |
| 5,752,513 A | 5/1998 | Acker et al. | 128/653.1 |
| 5,765,561 A | 6/1998 | Chen et al. | |
| 5,767,820 A | 6/1998 | Bassett et al. | 345/8 |
| 5,776,050 A | 7/1998 | Chen et al. | |
| 5,800,341 A | 9/1998 | McKenna et al. | |
| 5,825,908 A | 10/1998 | Pieper et al. | |
| 5,833,608 A | 11/1998 | Acker | 600/409 |
| 5,840,025 A | 11/1998 | Ben-Haim | 600/424 |
| 6,151,404 A | 11/2000 | Pieper | |
| 6,167,296 A | 12/2000 | Shahidi | 600/427 |
| 6,216,027 B1 * | 4/2001 | Willis et al. | 600/424 |
| 6,241,657 B1 | 6/2001 | Chen et al. | |
| 6,261,226 B1 | 7/2001 | McKenna et al. | |

* cited by examiner

METHOD FOR PRODUCING HIGH RESOLUTION REAL-TIME IMAGES, OF STRUCTURE AND FUNCTION DURING MEDICAL PROCEDURES

RELATED APPLICATIONS

This application claims benefit of provisional application Serial No. 60/118,765 filed on Feb. 5, 1999.

BACKGROUND OF THE INVENTION

The field of the invention is medical imaging, and particularly, the production of real-time anatomic images used to guide the performance of medical procedures.

High resolution medical images which accurately depict detailed anatomical features can be produced using a number of imaging modalities. Such images may be produced, for example, using electron beam CT systems, ultrasound systems or MRI systems commercially available from a number of manufacturers. To reconstruct high resolution and high SNR images, however, considerable data must be acquired. Such data acquisition requires time ranging from seconds to many minutes depending on the imaging modality used and the particular subject of the acquisition. For example, when imaging the human heart both cardiac and respiratory gating may be used during the data acquisition with the result that image data may only be acquired during short intervals during each respiratory and cardiac cycle. A high resolution 3D image of the heart may require many seconds or minutes to acquire using an MRI system or an x-ray CT system. Such high resolution images are commonly used for diagnosing disease, but they cannot be acquired and reconstructed at a high enough frame rate for use during medical procedures.

Medical images are produced at high frame rates for use during medical procedures. For example, x-ray fluoroscopy is commonly used by physicians to guide catheters in the placement of balloons and stents during angioplasty procedures. MR fluoroscopy is a method used to produce real-time images for monitoring medical procedures, and real-time ultrasound images are used in intravascular procedures such as those disclosed, for example, in U.S. Pat. Nos. 5,325,860 and 5,345,940. Such real-time imaging methods produce images at a frame rate of 10 to 30 frames per second to provide a relatively continuous, flicker-free view of the procedure being monitored.

While real-time medical images can thus be produced with a number of well-known imaging modalities, such images do not depict anatomy in great detail or with great clarity. They do depict medical instruments with enough clarity, however, that the instruments can be seen and guided to carry out some medical procedures.

There are medical procedures which require both real-time imaging to guide the operation and high resolution, high SNR depictions of the anatomical structures being operated upon. One such procedure is guided ablative therapy for cardiac arrhythmias. Ablative therapy employs an electrode which is placed on or near the heart wall and energized to create lesions of specific dimensions in specific anatomic locations. These lesions disrupt or change the sequence in which the heart wall muscle activates during an arrhythmia, and if done accurately, will prevent the arrhythmia from occurring.

As disclosed in U.S. Pat. Nos. 5,325,860 and 5,345,940, both the ablation electrode and an ultrasonic transducer may be delivered to the interior of the heart intravascularly by a catheter. The ablation electrode is guided into position using the real-time ultrasonic images and the ablation process is monitored using the real-time ultrasonic images. While this method and apparatus has enabled certain types of arrhythmias to be treated successfully, improved accuracy in the placement of the ablation electrode is required before the method can be used to treat many other cardiac arrhythmias. To do this, an accurate and clear image of the underlying anatomy must be provided in real-time to the physician so that the ablation electrode can be placed in precisely the right location.

SUMMARY OF THE INVENTION

The present invention is a method and means for providing clear, high resolution medical images in real-time, and more particularly, providing such medical images to assist physicians in the performance of medical procedures. The invention includes: acquiring image data of the subject anatomy and reconstructing an image which is a high resolution model of the subject anatomy; performing a medical procedure in which the subject anatomy is imaged in real-time by acquiring low resolution images at a high frame rate; registering the high resolution model of the subject anatomy with each acquired low resolution image; and displaying to the physician in real-time images of the registered high resolution model of the anatomy. The high resolution model may be a 2D or 3D image of static anatomy, or it may be a 4D model in which the fourth dimension depicts changes in the anatomy as a function of time, cardiac phase, respiratory phase, or the like. The creation of this model is performed using a high resolution imaging modality and it may be done prior to performing the medical procedure. The registration of the high resolution model is performed in real-time and includes a 2D or 3D spatial orientation as well as a registration in time or phase when the model depicts changing anatomy.

Another aspect of the present invention is the merging of real-time images of physiological data with an anatomical model during a medical intervention procedure. The physiological data may be, for example, electrophysiological data, EEG data or thermal data. If a medical device such as an endocardial electrode array is used, for example, the device itself may not be displayed. Instead, the location of each electrode in the array may be precisely located on the registered high resolution anatomic model and an electrical activation map is produced from the acquired electrophysiological data and overlayed on, or merged with the high resolution image. In a preferred embodiment the overlay is done by modulating the color of the pixels to indicate the activation timing of the imaged tissues, however other display methods may also be used.

Yet another aspect of the present invention is to accurately display the location of a medical device as a medical procedure is performed. The low resolution images clearly depict medical devices located within their field of view. Devices can thus be properly located in the displayed images by simply overlaying them on the registered high resolution model. In the case of an ablation catheter, for example, this overlay is simply the depiction of the device itself.

Yet another aspect of the present invention is the production of real-time medical images having a wide field of view. The field of view of many real-time imaging systems is very limited, or it may depict a single slice or a single projection view. It requires great skill and practice on the part of the physician to relate such limited views to the subject anatomy and properly understand the image. By registering the high resolution model of the anatomy to the limited real-time image, however, a much larger and more understandable field of view depicted by the model can be displayed. Indeed, the registered model may depict the subject anatomy in 3D and the images displayed to the physician can create a virtual reality environment during the medical intervention procedure.

The foregoing and other objects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

DESCRIPTION OF THE PREFERRED EMBODIMENT

The present invention is practiced by first producing a high resolution model of the anatomy of interest. This is done in the preferred embodiment described herein before the medical procedure is performed using appropriate medical imaging systems. In the preferred embodiment the anatomy of interest is the human heart, and particularly the walls of the heart chambers. A 4D model is produced which shows the patient's heart in three spatial dimensions at successive phases of the cardiac cycle. An MRI system is the imaging modality described below for producing this particular model, however, it can be appreciated by those skilled in the art that other imaging modalities such as electron beam CT or ultrasound may also be used. The particular modality used to produce the high resolution model will depend on many factors such as the equipment and expertise available, cost, and the particular anatomy of interest.

Figure 1:
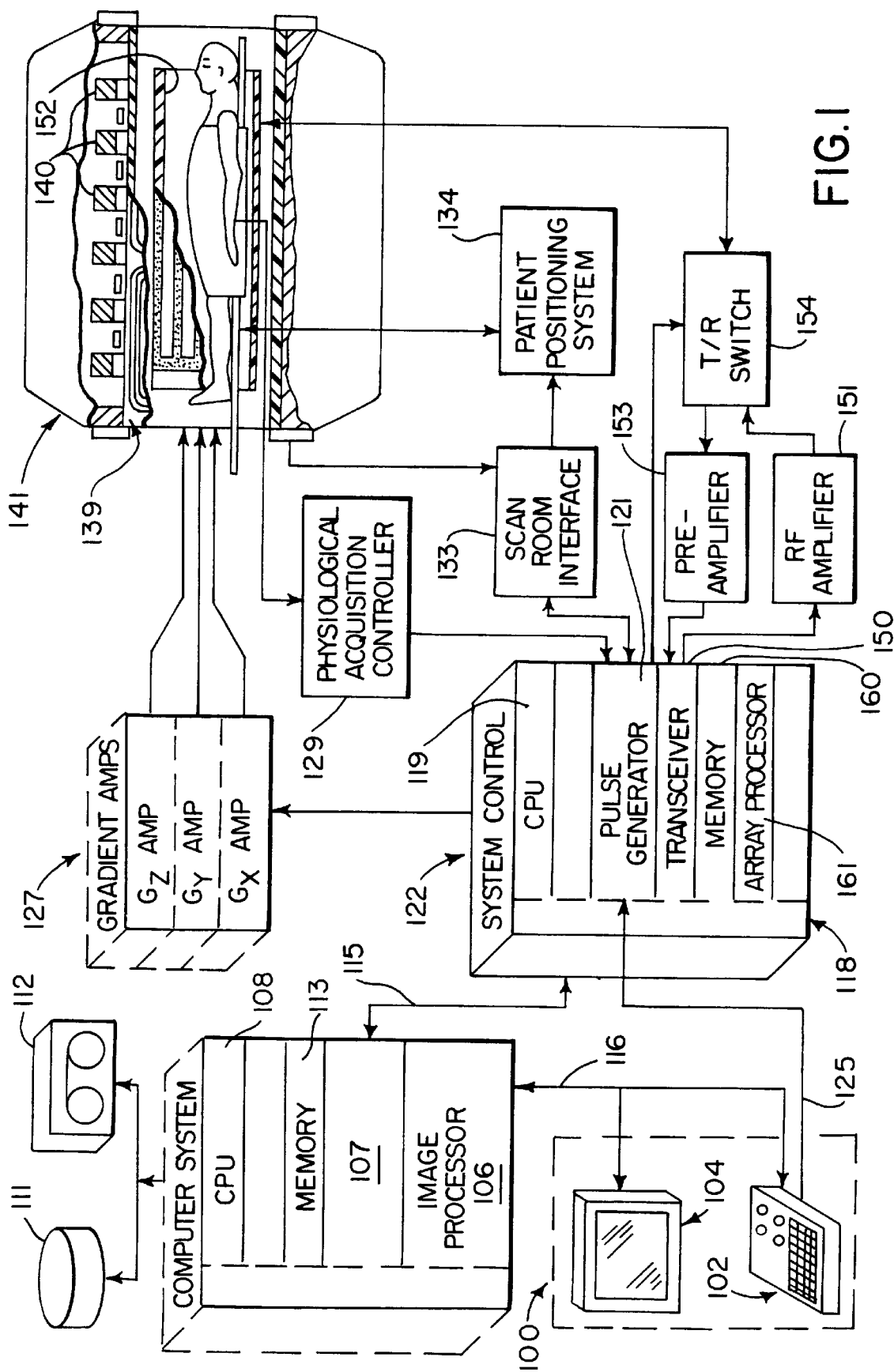
FIG. 1 is a block diagram of an MRI system used in the preferred embodiment to acquire high resolution images.

Referring first to FIG. 1, there is shown the major components of a preferred MRI system used to acquire data for the high resolution model. The operation of the system is controlled from an operator console 100 which includes a keyboard and control panel 102 and a display 104. The console 100 communicates through a link 116 with a separate computer system 107 that enables an operator to control the production and display of image on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 112 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred through a backplane 118 to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
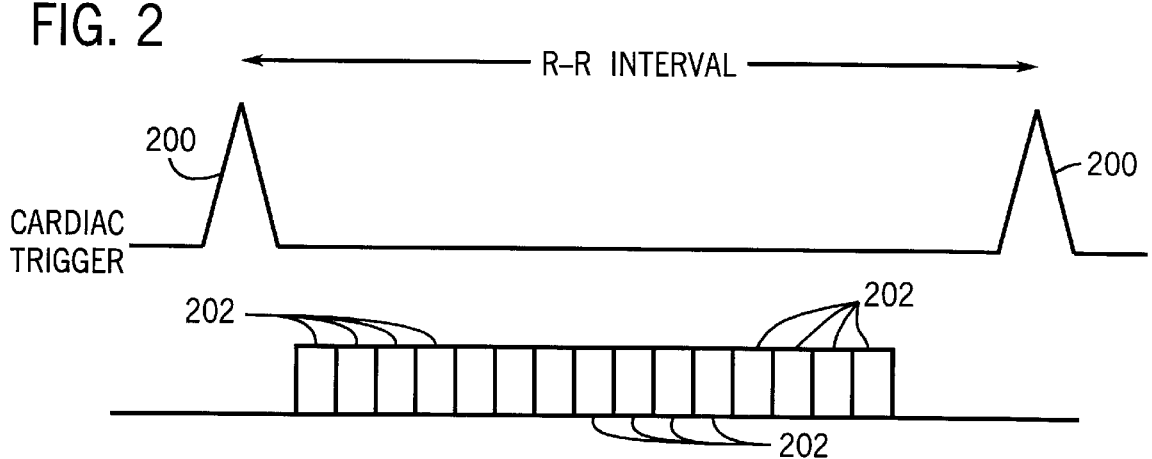
FIG. 2 is a graphic representation of a cardiac cycle illustrating acquisition of data by the MRI system of FIG. 1.

Referring particularly to FIG. 2, the cardiac acquisition in accordance with the preferred embodiment employs a series of fast gradient echo pulse sequences, which are performed under the direction of the pulse generator 121 with the repetition time, TR, of each gradient echo pulse sequence of between 6 and 15 ms, depending on the imaging parameters chosen. The data acquisition is cardiac gated by an ECG gating signal that triggers at the peak of the R wave in the QRS complex as indicated at 200. The pulse sequences are executed during the interval between the cardiac trigger signals 200 referred to as the R—R interval. The length of the R—R interval is a function of the patient's heart rate.

In a fast cardiac acquisition using gradient echoes, the R—R interval is divided up into many short segments, with each segment being a fast gradient acquisition pulse sequence with a nominal flip angle of between 20°–30°. Each fast gradient echo segment acquires an NMR signal representing a single line of k-space which is sometimes referred to as a view. Adjacent fast gradient echo segments are further combined into groups 202 where the data from each group 202 contributes to generating an image at different temporal phases of the cardiac cycle (R—R interval). The temporal location of these phase images depends on the relative time from the cardiac trigger (R-wave) 200 to the center of each group 202 of fast gradient echo segments. In the preferred embodiment fifteen groups 202 are acquired during each R—R interval, and from the resulting fifteen acquired k-space data sets, fifteen corresponding 2D slice images are reconstructed using a two-dimensional Fourier transformation in the well-known manner. These 2D slice images depict one slice through the heart at fifteen successive phases of the cardiac cycle.

The scan continues by acquiring additional slices through the heart. In the preferred embodiment 50 to 100 contiguous slices are acquired and reconstructed into 2D images. At the completion of the scan these 2D slice images are combined to form 3D image data sets. As a result, fifteen separate 3D image data sets are acquired in which the pixels indicate signal intensity in voxels throughout the patient's heart at fifteen successive cardiac phases.

As indicated above, the imaging modality used to produce the 3D image data sets is not limited to MRI. Other modalities such as electron beam CT or ultrasound may also be used to produce the required high resolution image data. An advantage of the present invention is that the high resolution 3D image data may be acquired prior to its use in a real-time medical procedure, and this eliminates many factors that would otherwise limit the choice of imaging modality.

While it is possible to use the fifteen 3D image data sets as a high resolution, dynamic model of the patient's heart, further processing is performed in the preferred embodiment to reduce the amount of processing required to display the model in real time. In addition, it is the surface of the heart walls in each chamber that is of interest in the medical procedure practiced with the preferred embodiment, and it is a rendering of these 3D surfaces on a 2D display that is of most use to the physician. The processing of the acquired 3D image data sets into a 4D model from which 3D heart wall surfaces can be rendered may be performed in the image processor 106 in the MRI system of FIG. 1, or it may be carried out on a separate work station. A work station such as the Model O2 commercially available from Silicon Graphics, Inc. of Mountain View, Calif., operating 3D software such as that commercially available under the trademark ANALYZE from the Mayo Clinic of Rochester, Minn. is preferred.

Figure 2A:
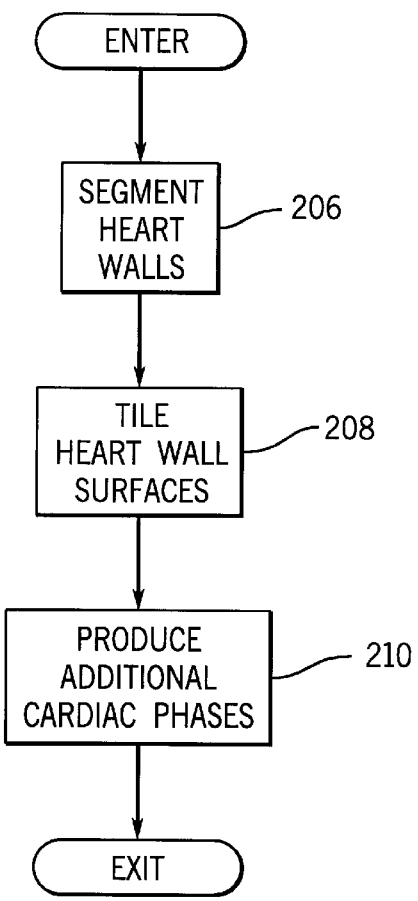
FIG. 2A is a flow chart of a process used to produce a 4D model of the subject anatomy from images acquired with the MRI system of FIG. 1.

Referring particularly to FIG. 2A the first step in this process is to segment the heart walls from the remaining structures as indicated at process block 206. As described in "Three-Dimensional Biomedical Imaging" by Richard A Robb, published in 1995 by VCH Publications, Inc., pp.166–169, segmentation produces a binary volume image data set in which all pixels located within a heart wall are set to "1" and all pixels outside the heart walls are set to "0". Segmentation can be performed by filtering and thresholding the 3D image data sets with user-specified thresholds, followed by 3D region filling initiated from appropriate starting points selected by the user. Many segmentation methods are known to those skilled in the art such as mathematical morphology and multi-spectral classification. This step may involve manual intervention and can require considerable time, but it is performed "off-line", before the medical procedure is started.

The next step indicated by process block 208 is to tile the surfaces of the segmented heart wall images. As described, for example, by Robb, R. A., S Aharon, B. M. Cameron: "Patient-specific Anatomic Models from Three Dimensional Medical Image Data for Clinical Applications in Surgery and Endoscopy," *Journal of Digital Imaging,* 10(3) (Suppl. 1-August):31–35, 1997, the tiling step specifies sets of x, y, z point locations on the segmented heart wall surfaces and connects them together to form adjacent polygons. In the preferred embodiment each polygon, or "tile", is a triangle defined by an x, y, z location and a unit vector which is perpendicular to the plane of the triangle. Surfaces defined by tiles can be rapidly transformed in location and orientation, making such a representation of the heart wall surfaces attractive for real-time processing.

The high resolution model of the patient's heart is produced from the fifteen tiled surface images by creating fifteen additional tiled surface images. This is accomplished at process block 210 by deforming the acquired tiled surface images. Such deformation, or "morphing" of 3D image data sets is a well known procedure and is described, for example, by Stacy, M., D. Hanson, J. Camp, R. A. Robb: "High Performance Computing In Biomedical Imaging Research at Mayo Clinic", *Parallel Computing,* 24:1287–1321, 1998. A dynamic 4D model of the patient's heart is thus produced in which tiled surfaces of the heart walls are depicted at successive increments of cardiac motion. If displayed in sequence, or played back as a function of time, a 3D high resolution picture of the beating heart is produced. The observer can be placed at any angle with respect to this dynamic image, and more importantly, the observer can be placed inside one of the heart chambers. Indeed, the dynamic heart model may be employed in a virtual reality system to place the physician inside the patient's heart during the medical procedure. Such virtual reality systems are well known to those skilled in the art as described, for example, Robb, R. A.,: "Virtual Reality Assisted Surgery Planning Using Patient Specific Anatomic Models", *IEEE Engineering In Medicine and Biology*, Ed., Metin Akay, 15(2):60–69, March/April, 1996, and the viewer can be made to feel that he is physically inside a heart chamber looking at the movement of the chamber walls as the medical procedure is performed.

It should be apparent to those skilled in the art that there are many other ways to produce the high resolution model of the subject anatomy. The image data can be acquired by imaging modalities such as x-ray CT, electron beam CT, ultrasound or magnetic resonance imaging. The high resolution model may also take a number of different forms depending on the subject anatomy and the particular medical procedure to be performed. The high resolution model may be as simple as a single 2D image or a single 3D image of static anatomy, or it may depict 3D dynamic structures or surfaces as described above. In addition, the dynamic 3D model disclosed above is comprised of a large number of 3D data sets representing tiled surfaces at successive increments of cardiac motion. A dynamic 3D model can also be produced with far fewer 3D data sets (e.g. one depicting the heart at systole and a second depicting the heart at diastole) if equations are used to define the deformation of the tiled surfaces that occurs during the cardiac cycle.

The medical procedure performed using the preferred embodiment of the invention is intracardiac electrophysiology. This procedure involves the display of an electrical activation map which indicates the timing of the electrical signals that activate the muscles in the patient's heart chamber walls. Such electrical activation maps indicate abnormalities in the activation which cause cardiac arrhythmias. The second part of the procedure is to ablate heart wall tissue with an endocardial ablation device to correct such abnormalities. The system for performing this procedure is shown in FIGS. 3–5.

Figure 3:
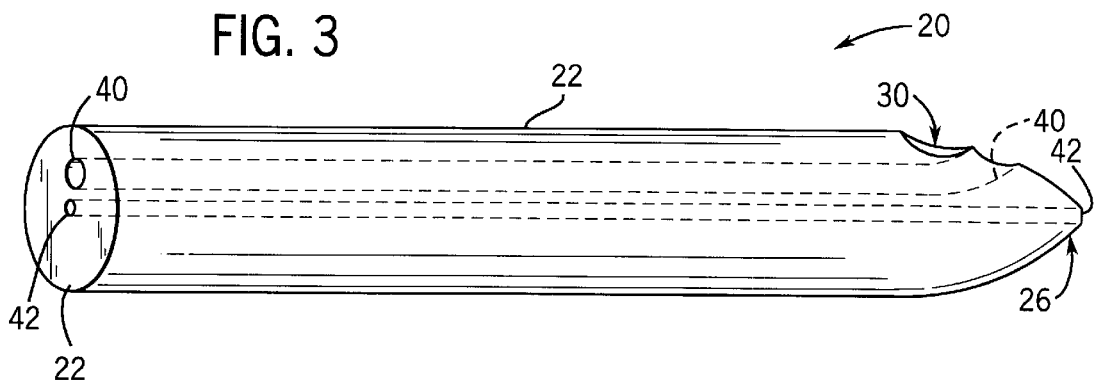
FIG. 3 is a partial view of a catheter showing its distal end.
Figure 4:
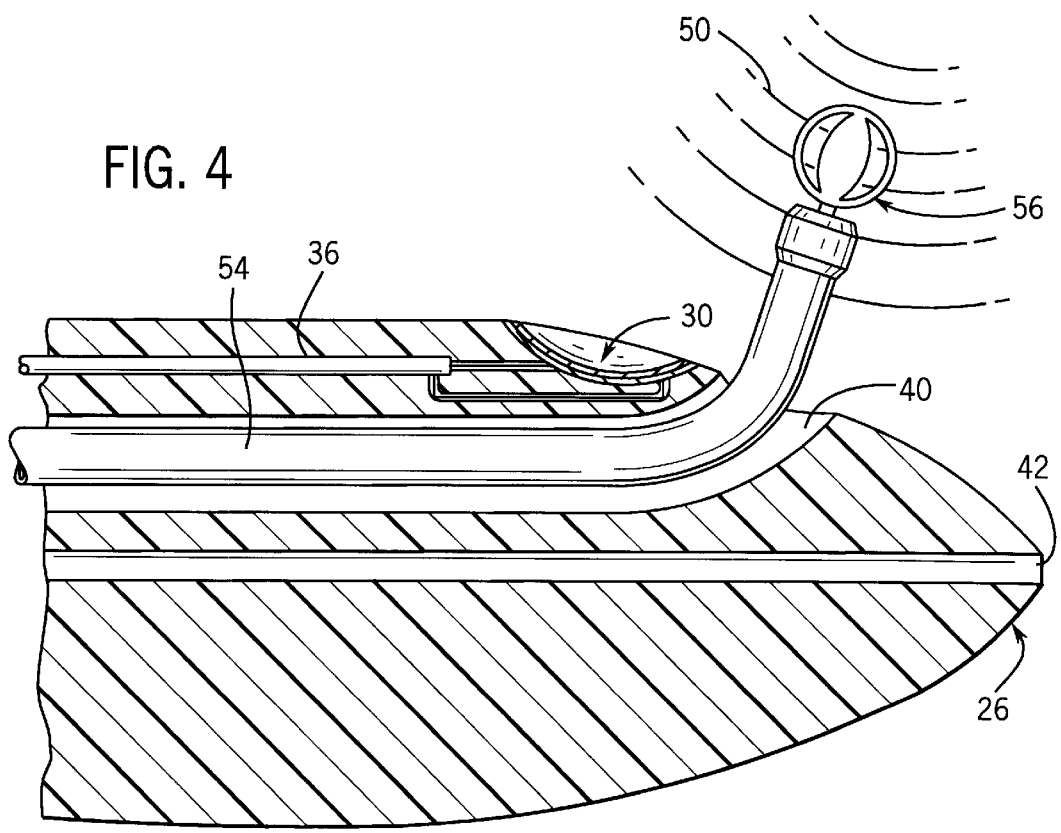
FIG. 4 is a partial view of the catheter of FIG. 3 showing its distal end in more detail supporting an ablation device.
Figure 5:
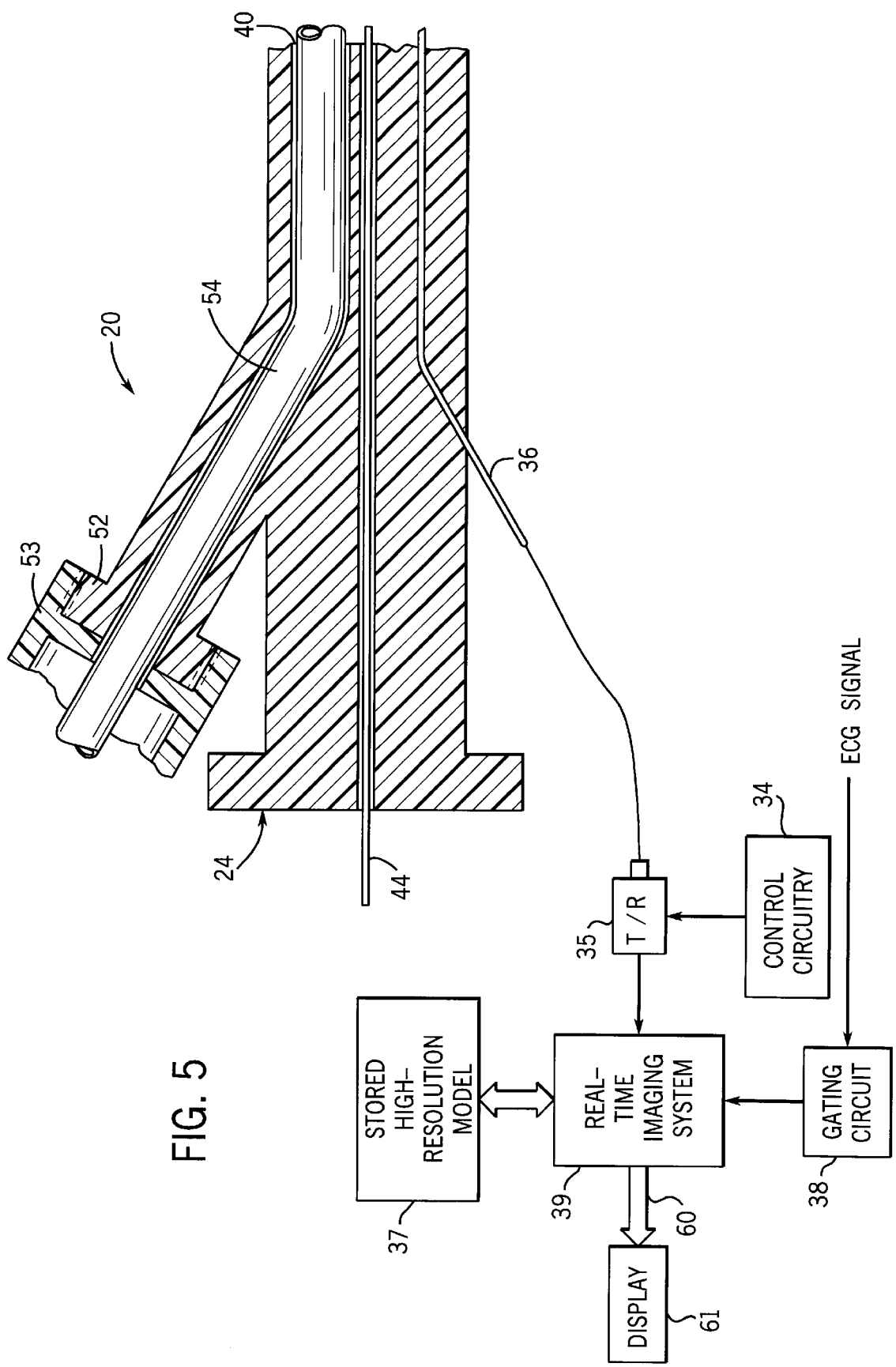
FIG. 5 is a schematic representation of the proximal end of the catheter of FIGS. 3 and 4 connected to an imaging system.
Figure 6:
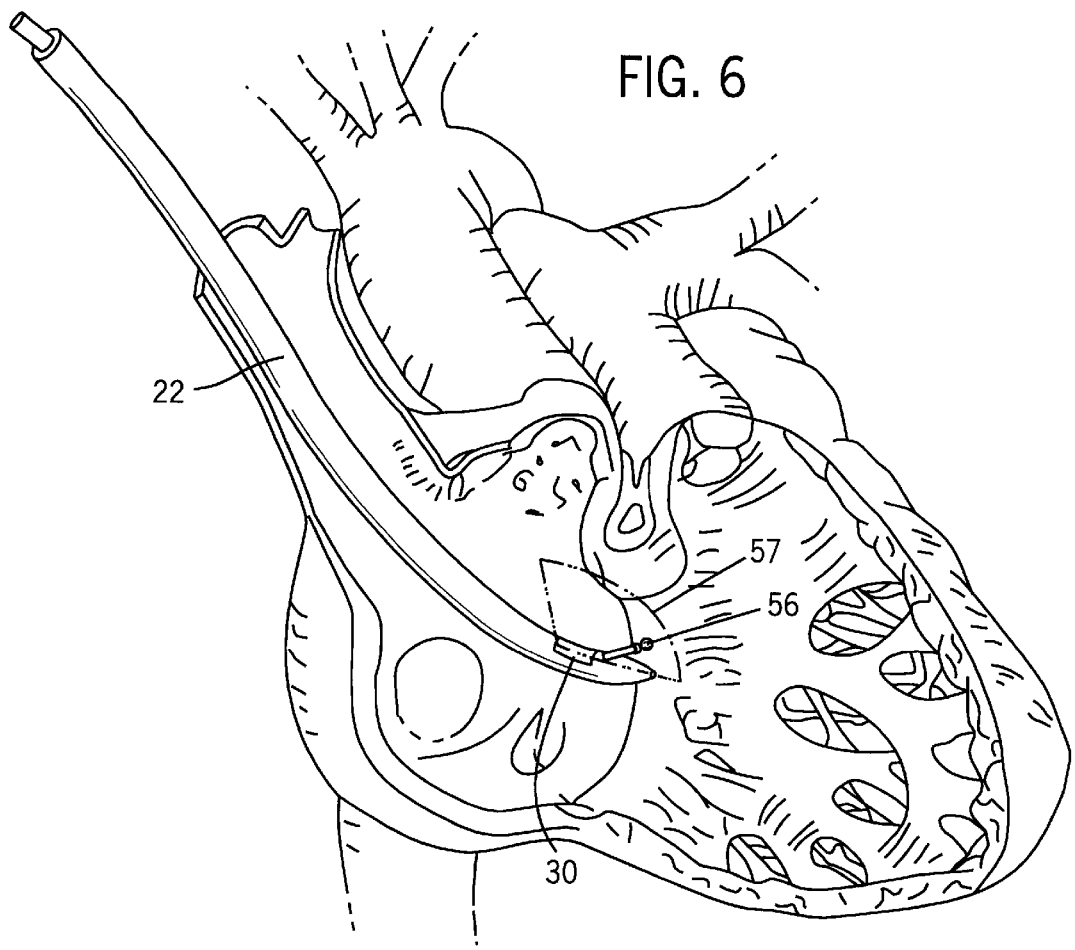
FIG. 6 is a pictorial representation of the distal end of the catheter in a patient's heart during a medical procedure.

Referring now to FIGS. 3–5, there is, generally illustrated by reference numeral 20, a catheter 20 which includes an elongated flexible plastic tubular catheter body 22 having a proximal end 24 and a distal end 26. Catheter 20 includes proximate its longitudinal distal end 26 a phased array ultrasonic transducer 30 which is used to transmit ultrasound and receive resultant echoes so as to provide a field of view within which features can be imaged. It is appreciated that other types of ultrasonic transducers can be used, such as mechanical types, or dynamic array types, or any offset stereoscopic imaging types, or any multidimensional imaging types incorporated into a virtual reality environment for underblood operation. An electrical conductor 36 is disposed in the catheter body 22 for electrically connecting transducer 30 to control circuitry 34 external of catheter body 22, and it extends from proximate the proximal end 24 of catheter body 22 to proximate the distal end 26 of the catheter body 22. An access port 40 also extends the length of the catheter body 22 and it is configured to receive a therapeutic device, so as to enable such items to be delivered via access port 40 to distal end 26 of catheter body 22 for operation within the ultrasonic transducer field of view. A guide wire access port 42 is also disposed within catheter body 22 and extends from the proximal end 24 of the catheter body 22 to the distal end 26 of catheter body 22 for receiving a guide wire 44. As is well known in the art, the guide wire 44 may be fed by the physician through the vasculature and into the patient's heart. The catheter body 22 is then fed along the guide wire 44 until its distal end 26 is inside the heart as shown in FIG. 6. The guide wire 44 may then be withdrawn.

In the preferred embodiment the ultrasonic transducer has a frequency of 5 to 20 megahertz (MHz). Intracardiac imaging in an adult requires image penetration of up to 20 centimeters (cm). Catheter body 22 has a diameter of 4 to 24 French [one French divided by Pi equals one millimeter (mm)]. Access port 40 has a diameter of 7 to 8 French and guide wire port 42 has a diameter of 0.025 to 0.038 inches. For a detailed description of the catheter 20, reference is made to U.S. Pat. No. 5,345,940 which is incorporated herein by reference.

As illustrated in FIG. 5, control circuitry 34 is electrically interconnected to a transceiver circuit 35 (T/R) for receiving and transmitting signals via cable 36 connected to ultrasonic transducer 30. During operation, control circuitry 34 causes ultrasonic transducer 30 to vibrate so as to cause an appropriate ultrasound wave to project from the distal end 26 of catheter body 22. The ultrasound wave, represented by lines 50 in FIG. 4 is propagated through the blood surrounding distal end 26 and a portion of the body structure. A portion of the ultrasound wave so transmitted is reflected back from the body structures to impinge upon transducer 30. An electrical signal is thereby generated and transmitted by the cable 36 to the input of transceiver 35.

As will be described in detail below, the ultrasonic image data is input to a real-time imaging system 39 which uses the real-time ultrasound image data, the high resolution model of the patient's heart stored in memory 37 and an ECG signal from the patient to produce real-time images which are output through cable 60 to a display 61. The imaging system 39 is a computer workstation containing a fast microprocessor, large hard disk for storing image data and software for implementing the present invention. In the preferred embodiment a work station such as the Model O2 commercially available from Silicon Graphics, Inc. of Mountain View, Calif. and having an R10000, 175 MHz processor is employed. Imaging occurs while a therapeutic or surgical device is being used at distal end 26 of catheter 20 within the field of view provided by ultrasonic transducer 30. The user can thus monitor the medical procedure as it is being performed.

As illustrated in FIG. 5, catheter body 22 includes proximate its proximal end 24 a mounting structure 52 to the access port 40. An ablation device structure 53 is attached to mounting structure 52 and an elongated cable-like member 54 extends along access port 40 and slightly beyond distal end 26 of catheter body 22. An operative portion 56 of the ablation device 53 is attached to this distal end.

Figure 7:
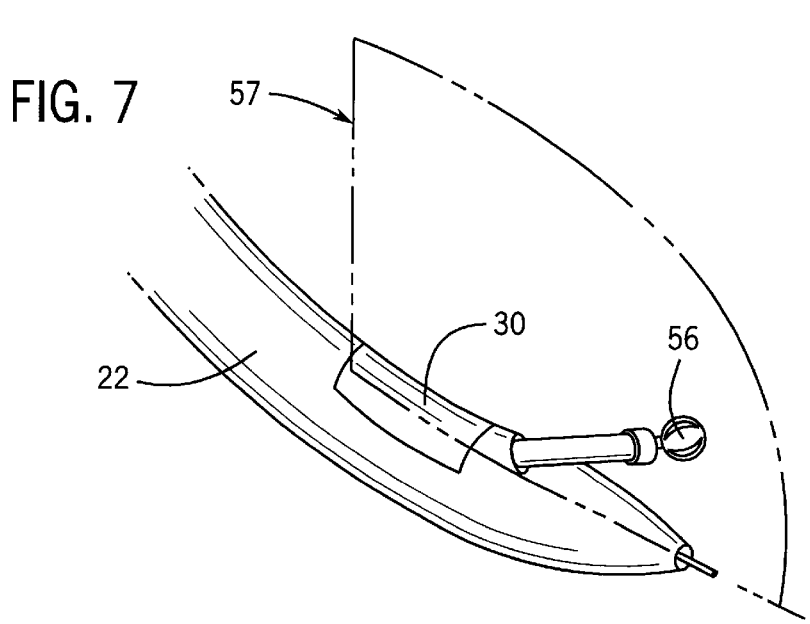
FIG. 7 is a pictorial representation of the distal end of the catheter in FIGS. 3–6 showing the field of view of an ultrasonic transducer mounted therein.

As illustrated in FIGS. 6 and 7, the physician inserts the flexible catheter body 22 into the patient via the appropriate vascular access to the desired location where the subject anatomy, such as a heart chamber, can be operated upon. In the example shown, the distal end of the catheter 22 is inserted into the right atrium and right ventricle where the ablation device 56 can be used to treat cardiac arrhythmias. The operational portion 56 of the ablation device is in the field of view of ultrasonic transducer 30, and it is possible for the physician to monitor its operation. Moreover, the physician can monitor the features of the heart wall within the field of view before, during and after interventional activity. As indicated by lines 57, the field of view of the ultrasonic transducer 30 is limited to a small fraction of the surrounding wall of the heart chamber. The quality of the real-time ultrasonic images is also limited.

Referring again to FIG. 5, as the physician carries out the medical procedure the ultrasonic transducer 30 produces image data at a frame rate of 30 images per second. As will now be described, the real-time imaging system 39 employs these real-time image frames along with an ECG signal from the patient to register the stored high resolution heart model 37. The registered high resolution model is then used to produce high resolution, large field of view images in real-time on the display 61.

Figure 8:
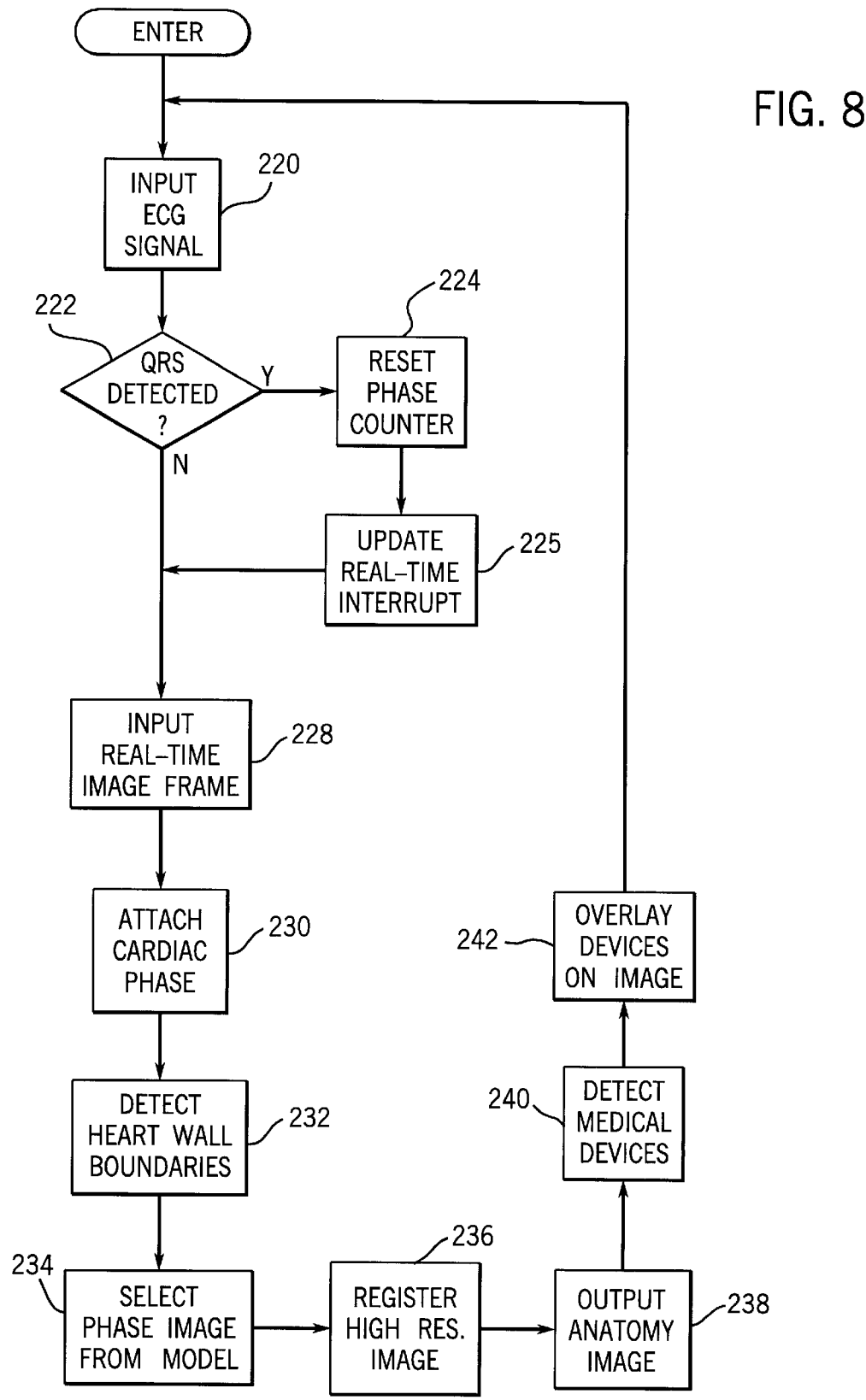
FIG. 8 is a flow chart of the process performed by the real-time image processor which forms part of the imaging system in FIG. 5.

Referring particularly to FIGS. 5 and 8 the software in the real-time imaging system 39 inputs a gating signal 200 from a gating circuit 38, as indicated at process block 220. The gating circuit 38 receives the ECG signal from the patient, and using methods well known in the art, detects the peak in the R wave of the QRS complex. Such methods are described, for example, in U.S. Pat. Nos. 3,939,824; 4,259, 966 and 4,181,135. When the gating signal 200 is detected as determined at decision block 222, the system branches to reset a cardiac phase counter at process block 224. The cardiac phase counter maintains an indication of cardiac phase and it is periodically incremented by a real time interrupt during each cardiac cycle. The interval between timed interrupts is determined at process block 225 using the patient's heart rate, as measured by the average of the previous 5 R—R intervals.

As indicated by process block 228, the latest real-time image frame from the ultrasonic transducer 30 is then input and the current value of the cardiac phase counter is read and appended to the image as indicated at process block 230. This is accomplished by reading the current value of the cardiac phase counter and storing it in a memory location associated with the image frame. The real-time image is then processed to put it into a form which can be used with the registration process. In the preferred embodiment this includes detecting the heart wall boundaries in the real-time image as indicated at process block 232. This may be accomplished using a number of well known feature detection methods, such as the boundary detection method disclosed in co-pending U.S. pat. appl. Ser. No. 08/935,128, filed on Sep. 22, 1997 and entitled "Fast Cardiac Boundary Imaging" which is incorporated herein by reference.

As indicated at process block 234, the proper high resolution image is then selected from the stored 4D model. This is accomplished using the stored phase counter value which indicates which phase of the cardiac cycle the heart was in at the moment the current real-time image frame was acquired. As indicated above, the 4D model stores 3D high resolution images that depict the heart at successive positions during the cardiac cycle and the nearest one is selected. It should be apparent that in the preferred embodiment the 4D model stores a large number of images (e.g. 30) and this step is merely the selection of the cardiac phase image which is closest to the value indicated by the phase counter. If fewer cardiac phase images are stored, however, it is also possible to interpolate between the nearest two phase images to produce a high resolution cardiac image that depicts the heart at the precise moment indicated by the phase counter.

The selected high resolution image is then registered with the current real-time image frame as indicated at process block 236. The preferred method for registering the two image data sets is described in U.S. Pat. No. 5,568,384 which issued on Oct. 22, 1996 and is entitled "Biomedical Imaging And Analysis", and which is hereby incorporated by reference. As described in more detail therein, this is an iterative process in which a match image (the stored 4D model) is translated, rotated and scaled to provide the best registration possible with a base image (the real-time image frame). Successive transformations of the match image are made and a cost function is calculated after each. The cost function is calculated as the root mean square (r.m.s.) average of the distances from points on the transformed match image to corresponding points on the base image. Registration is achieved with the transformation that results in a global minimum in the cost function. Convergence to this result is speeded by beginning with low resolution versions of both images and registering successively high resolution images. This process is implemented in the preferred embodiment using the "chamfer matching" feature on the commercially available 3D imaging system identified above and sold under the trademark ANALYZE.

It should be apparent to those skilled in the art that other methods for registering known images may be employed, such as the method known in the art as "voxel matching" and the methods disclosed in U.S. Pat. Nos. 5,839,440; 5,531, 520 and 5,706,416.

The registered high resolution image of the heart wall anatomy is output to the display 41 as indicated at process block 238. Such a display can be a relatively simple 2D representation of a portion of the heart wall within the field of view of the ultrasonic transducer, or it can be a more expansive view. Indeed, as indicated above, the field of view can surround the viewer and provide an image which places the physician inside the heart chamber.

The real-time ultrasonic transducer images include not only the subject anatomy, such as a portion of the heart wall, but also the medical device. As described above, in the preferred embodiment the medical device is an ablation device 56 which is manipulated within the field of view of the ultrasonic transducer 30. The echo signals received from medical devices are acoustically distinctive and can be automatically or manually detected in the reconstructed real-time images. As indicated at process block 240, the location of the medical device is output to the display 41 to overlay the anatomical image as indicated at process block 242. The medical device overlay can be an image of the device, an icon that represents the device, or simply a cursor or cross-hairs.

The process indicated in FIG. 8 continues throughout the medical procedure to provide the physician with a continuously updated image of the subject anatomy and the medical device. The displayed image is updated at a frame rate sufficiently high to provide a continuous view of the interior of the beating heart and the movement and placement of the ablation electrode. Because a high resolution and large field of view image is presented, it is easy for the physician to identify the portion of the heart wall that requires treatment and to more accurately manipulate the ablation device into position.

The display 61 can take a number of different forms depending on the medical procedure being performed and the preferences of the physician. In the preferred embodiment the center of the field of view of the acoustic transducer is aligned in the center of a large CRT or LCD display. Different parts of the anatomy may be viewed by moving the catheter distal end 26 to "aim" the acoustic transducer at the anatomic structures of interest. In the alternative a joystick, (not shown in the drawings) may be used to scan away from the field of view of the ultrasonic transducer when other parts of the anatomy are to be examined without moving the catheter. The orientation of the observer within the anatomic structure (e.g. heart chamber) is maintained using navigation icons as described in co-pending U.S. pat. appln. Ser. No. 08/982,014 filed on Dec. 1, 1997 and entitled "Graphic Navigational Guides For Accurate Image Orientation and Navigation".

Figure 11:
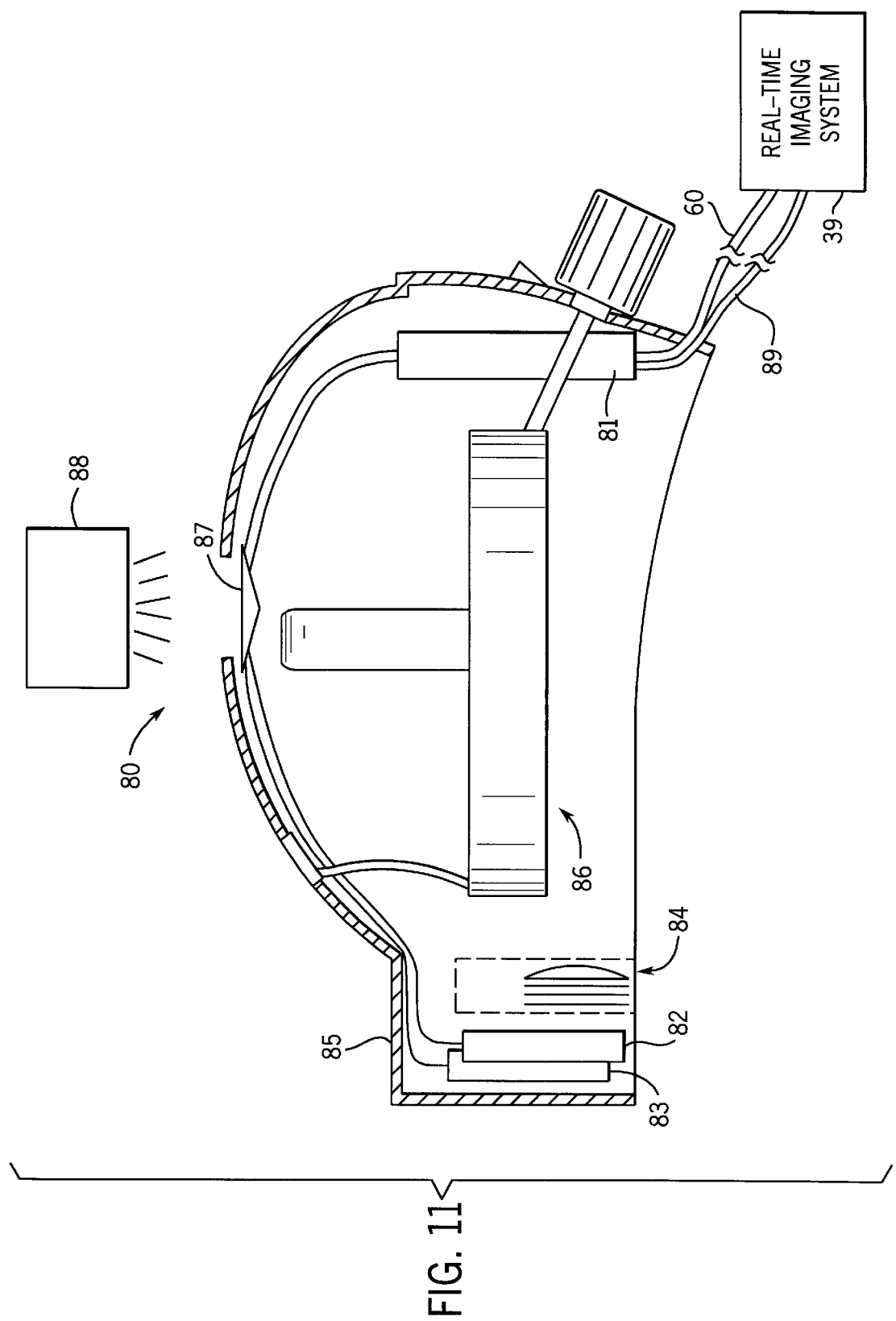
FIG. 11 is a pictorial representation of a head mounted virtual environment display device.

An alternative embodiment of the invention employs a head mounted display such as that shown in FIG. 11 to provide a virtual environment for the physician. The display includes a helmet 80 which is connected to the real-time imaging system 39 through cable 60. Drive circuitry 81 mounted in the back of the helmet 10 receives video signals from the imaging system 39 and converts them into image frames. Color LCD displays 82 and 83 display the image frames through optics 84 to the eyes of the viewer. The LCD displays 82 and 83 and the optics 84 are mounted in a frame in front portion 85 of the helmet 10. A circular headband 86 is mounted to the interior of the helmet 10 and fits around the viewers head to hold the helmet 10 firmly, but comfortably in place with the optics 84 aligned over the viewers eyes.

A head position sensor 87 is mounted in the top of the helmet 10 to sense the orientation of the helmet with respect to a chosen reference orientation. The sensor 87 includes a receiver which receives ultrasonic waves through an opening in the top of the helmet. The ultrasonic waves are produced by a transmitter 88 mounted above the operating table. Signals from the ultrasonic sensor 87 are conveyed through cable 89 where they are processed to produce joystick signals that move the field of view of the images produced by LCD displays 82 and 83. When the physician's head is in the selected reference orientation, the center of the displayed image corresponds with the center of the field of view of the catheter ultrasonic transducer 30. As the physician's head rotates to the left or right, up or down, the center of the displayed image rotates a corresponding amount. Thus, the physician can look at anatomic features far outside the field of view of the catheter ultrasonic transducer 30. For a more detailed description of the head mounted display, reference is made to U.S. Pat. No. 5,321,416 entitled "Head-Mounted Visual Display Apparatus" which is incorporated herein by reference.

Another aspect of the present invention is the display of a physiologic parameter or process. In the preferred embodiment this physiologic parameter is activation time which is presented in the spatial form of an electrical activation map. As indicated above, such activation maps are functional images used to identify regions of the heart wall that are causing cardiac arrhythmias.

Figure 9:
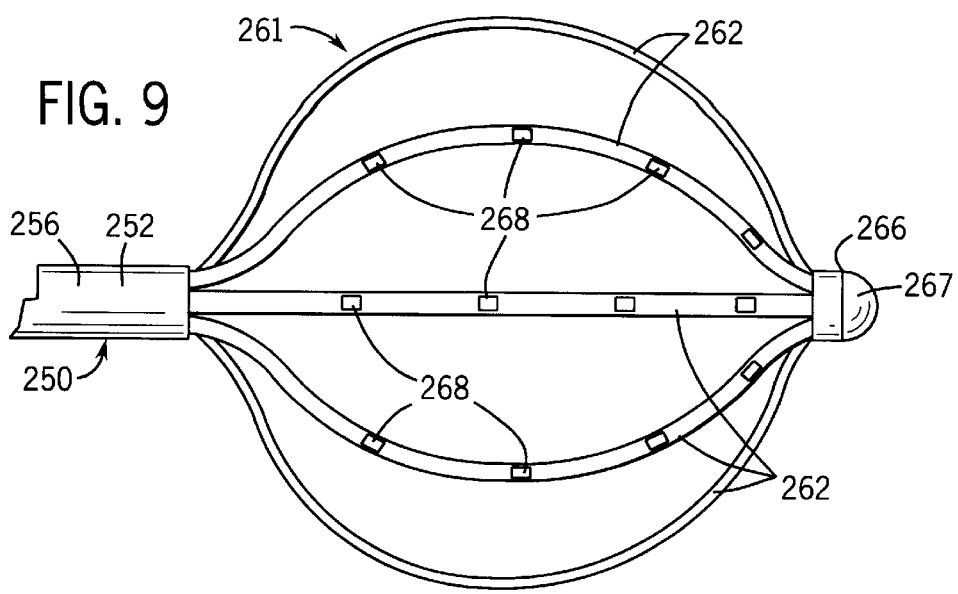
FIG. 9 is a pictorial representation of part of a mapping catheter.
Figure 10:
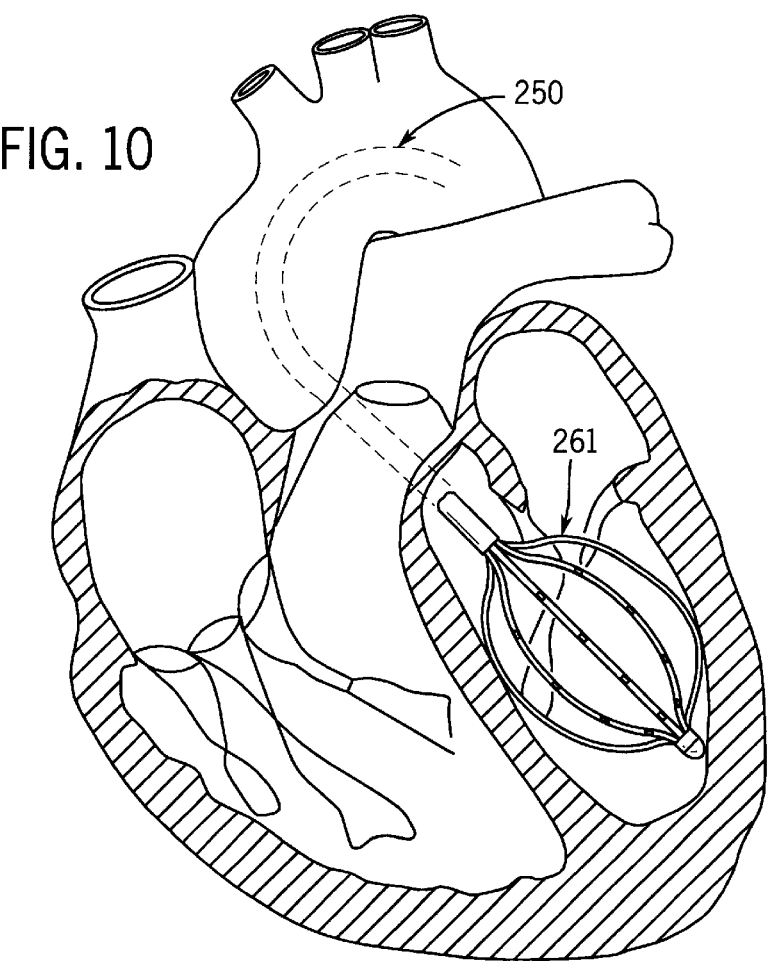
FIG. 10 is a pictorial representation of the imaging catheter placed in a heart chamber.

As shown in FIGS. 9 and 10 data for producing an activation map is acquired using a mapping catheter 250. The mapping catheter consists of a flexible shaft 252 having proximal and distal extremities. The flexible shaft 252 is in the form of an elongate flexible tubular member formed of a suitable plastic material such as a polyester. It is provided with a lumen 256 extending there through, although it can also have a multilumen configuration.

An electrode assembly 261 in the form of a basket is mounted on the distal extremity of the shaft 252. It is provided with a plurality, as for example, eight circumferentially spaced apart longitudinally extending arms 262 having proximal and distal extremities. As shown, the arms 262 have an outwardly bowed shape memory and have their proximal extremities secured to the distal extremity of the shaft 252. The distal extremities of the arms 262 are interconnected at a hub 266 having a rounded forward extremity 267.

A plurality of electrodes 268, as for example, four are formed on the outer surface of each of the arms 262. The electrodes 268 are spaced longitudinally along the arms 262 and are insulated from each other. They are connected to conductors in a suitable multi-conductor strip such as a ribbon cable (not shown) which extends through the lumen 256 in the shaft 252. The electrodes 268 are capable of sensing electrical signals which are generated in the wall of the heart. These electrical signals pass through the ribbon cable to the proximal end of the mapping catheter 252 where they are connected to circuitry which records the timing of the signals sensed by each electrode 268. Circuitry such as that disclosed in U.S. Pat. No. 5,156,151 and commercially available from Arrhythmia Research Technology is used for this purpose.

As described in U.S. Pat. No. 5,465,717 which issued on Nov. 14, 1995 and is entitled "Apparatus And Method For Ventricular Mapping And Ablation", and which is incorporated herein by reference, the electrode assembly 261 is guided through arteries and into a chamber of the heart. A guiding catheter (not shown) is used for this purpose and when the guiding catheter is withdrawn a short distance to expose the basket assembly 261, the arms 262 bow radially outward to press the electrodes 268 against the heart chamber walls. The electrical signals produced by the electrodes 268 indicate the relative timing of the signals that contract the heart wall muscles during the cardiac cycle. As described in U.S. Pat. No. 5,409,000 which issued Apr. 25, 1995 and is entitled "Endocardial Mapping And Ablation System Utilizing Separately Controlled Steerable Ablation Catheter With Ultrasonic Imaging Capabilities And Method", the separate electrodes 268 are encoded with ultrasonic markers. The markers are air bubbles formed in each arm 262 to produce bright spots in ultrasonic images. The number of air bubbles/bright spots indicates the identity of the electrode 268.

There are many different commercially available devices for endocardial mapping. Such alternative mapping devices are available from Biossense, Inc. of Orangeburg, N.Y.; Cardiac Pathways Corporation of Sunnyvale, Calif.; and Endocardial Solutions, Inc. of St. Paul, Minn. Such mapping devices are disclosed in U.S. Pat. Nos. 5,568,809; 5,345,936; 5,228,442; 5,507,802; 5,558,073; and 5,662,108.

The production of the electrical activation map using the electrode assembly 261 can be performed in real-time as the ablation procedure is performed. The electrode assembly 261 is inserted into the subject heart chamber as illustrated in FIG. 10 and the mapping data is acquired. The ablation procedure is then carried out using the ablation device 56 shown in FIG. 6 and activation map produced from the mapping data. The ablation device and associated ultrasonic transducer is inserted through the lumen 256 in the catheter shaft 252 and is separately manipulated by the physician to carry out the ablation procedure while real-time ultrasonic images are acquired as described above. Such a catheter is described, for example, in U.S. Pat. No. 5,409,000 entitled "Endocardial Mapping and Ablation System Utilizing Separately Controlled Steerable Ablation Catheter with Ultrasonic Imaging Capabilities and Method".

The locations of the mapping basket electrodes 268 are detected in the acquired ultrasonic images and the locations of the electrodes 268 are registered with the high resolution image displayed for the physician. This is done by aiming the transducer 30 at each electrode 268, placing a cursor on an electrode pictured in the image, and typing in the electrode number indicated on the image by the number of bright spots. When all of the electrode positions have been entered, an electrical activation map may be produced on the high resolution image.

The electronic activation map is produced by color coding the displayed heart wall tiles with the timing data acquired with the mapping catheter. In other words, the electronic activation map is overlaid as color coding on the detailed anatomical image as indicated at process block 242 This is accomplished by assigning the activation time measured at each basket electrode 268 to its corresponding location in the registered high resolution 3D image. That is, locations on the image of the heart wall surface corresponding to basket electrode locations are assigned measured activation times. The activation times of other locations on the heart wall surface are then computed by averaging the activation time of the nearest "n" neighbor basket electrodes as weighted by their Euclidian distance from that location. Activation times for every location/pixel on the heart wall surface is thus calculated and then the range of activation times is divided into 20 successive time intervals. Twenty separate bands of pixels, each with activation times in the same time interval, are then color coded with the same color. Using color as a representation of time, activation wave fronts are thus overlayed by coloring the pixels in the registered high resolution image of the heart wall.

It should be apparent to those skilled in the art that the registered physiological data can be displayed on the high resolution image in other ways. For example, the gray scale may be modulated rather than color, or the texture of the image may be used to indicate the physiological parameter being measured. Also, the physiological data may be displayed directly as numbers placed on the displayed anatomic structures.

When performed concurrently with the ablation procedure, the electronic activation map is updated continuously as ablation is performed. As a result, the physician can see by the changing pattern of the colored activation wave fronts the precise affect ablation is having on cardiac activation.

What is claimed is:

1. A method for producing cardiac images during a medical procedure on a subject, the steps comprising:
   a) acquiring image data of the subject's heart during successive cardiac phases;
   b) reconstructing a high resolution model image of the subject's heart from the acquired image data depicting the heart during successive cardiac phases of its functional cycle;
   c) acquiring low resolution images of the subject anatomy as the medical procedure is being performed;
   d) detecting the cardiac phase as the medical procedure is being performed;
   e) registering the high resolution model image with acquired low resolution images as the medical procedure is being performed using the detected cardiac phase; and
   f) displaying high resolution images during the medical procedure which employ the registered high resolution model image.

2. The method as recited in claim 1 in which the low resolution images include a medical device in their field of view and the medical device is displayed during the medical procedure by overlaying a depiction of the medical device on the higher resolution images.

3. The method as recited in claim 2 in which the medical device is an ablation device.

4. The method as recited in claim 2 in which the low resolution images are acquired with an ultrasonic transducer inserted into a chamber of the heart.

5. The method as recited in claim 4 in which the medical device is an ablation device inserted into the heart chamber.

6. The method as recited in claim 4 in which the medical device is an electrode assembly inserted into the heart chamber that produces electrical signals.

7. The method as recited in claim 6 in which the electrical signals produced by the electrode assembly are depicted on the high resolution images as activation wave fronts which indicate the timing of signals sensed on a heart chamber wall by the electrode assembly.

8. The method as recited in claim 7 in which the spatial distribution of the activation wave fronts are indicated by different colors.

9. The method as recited in claim 1 in which the high resolution images are depictions of three-dimensional anatomic surfaces.

10. The method as recited in claim 9 in which step e) is performed using a two-dimensional display device.

11. The method as recited in claim 9 in which step e) is performed using a three-dimensional display device.

12. The method as recited in claim 9 in which step e) is performed using a head mounted display.

13. The method as recited in claim 12 in which the anatomic surfaces that are depicted by the head mounted display is determined in part by the spatial orientation of the head mounted display.

14. The method as recited in claim 1 in which the low resolution images are acquired using a transducer having a limited field of view of the subject's heart and the displayed high resolution images depict a larger field of view of the subject's heart.

15. The method as recited in claim 14 in which the particular part of the subject's heart depicted in the displayed high resolution images is determined by the images acquired by the transducer.

16. The method as recited in claim 1 in which the high resolution model image depicts the subject's heart at discrete phases of the functional cycle.

17. The method as recited in claim 1 which includes selecting from the high resolution model image a depiction of the subject's heart at the detected cardiac phase.

18. The method as recited in claim 16 which includes detecting the cardiac phase as each low resolution image is acquired and the registration in step e) includes producing a depiction of the patient's heart by interpolating between two of the discrete phases depicted in the high resolution model image.

19. The method as recited in claim 1 in which an electrode assembly inserted into the heart produces electrical signals which indicate the timing of signals sensed on a heart chamber wall and the method includes:
   locating the electrode assembly in the acquired low resolution images; and
   depicting the signal timing measured by the electrode assembly on the displayed high resolution images.

20. The method as recited in claim 19 in which the signal timing is depicted by color coding the displayed high resolution images.

21. The method as recited in claim 19 in which the signal timing is depicted by texture coding of the displayed high resolution images.

22. The method as recited in claim 19 in which the signal timing is depicted by the gray scale of the displayed high resolution images.

23. A method for performing a medical intervention procedure on a subject using a medical device, the steps comprising:
   a) producing an anatomical image of the subject with a medical imaging system and updating the anatomical image in real-time as the medical intervention procedure is performed by periodically acquiring a low resolution image of the subject which depicts the medical device;
   b) acquiring physiological data from the subject with the medical device;

c) spatially registering the physiological data with the anatomical image by spatially registering a low resolution image acquired at substantially the same time as the physiological data is acquired with the anatomical image to thereby locate the medical device therein;

d) producing an output image which merges the spatially registered physiological data with the updated anatomical image; and e) repeating steps b), c) and d) during the medical intervention procedure to display physiological changes in the subject as the intervention procedure is performed.

24. The method as recited in claim 23 in which the medical device is an endocardial mapping device and the physiological data is electrophysiological data.

25. The method as recited in claim 24 in which the spatially registered physiological data is an electrical activation map that overlays the updated anatomical image.

26. The method as recited in claim 23 in which the anatomic image is produced by acquiring a series of high resolution images that depict the subject as it changes as a function of time during a functional cycle.

27. The method as recited in claim 26 in which the anatomic image is updated by selecting a high resolution image based on information indicative of the functional cycle at the time it is updated.

28. A method for performing a medical procedure on a subject which moves in a repetitive functional cycle, the steps comprising;

a) acquiring image data of the subject during successive phases of the functional cycle prior to performing the medical procedure;

b) reconstructing a model image of the subject which depicts the subject at successive phases of the functional cycle;

c) storing the model image;

d) acquiring images of the subject as the medical procedure is being performed;

e) detecting the phase in the functional cycle of the subject as the medical procedure is being performed; and f) producing images as the medical procedure is being performed by:
   i) selecting from the stored model image an image which depicts the subject at the currently detected functional cycle phase;
   ii) registering the image selected in step i) with the image currently acquired in step d);
   iii) displaying the registered image; and
   iv) repeating steps i), ii), and iii).

29. The method as recited in claim 28 which includes acquiring physiological data from the subject with a medical device during the medical procedure and the location of the medical device with respect to the subject is depicted in the images acquired in step d).

30. The method as recited in claim 29 in which the medical device is an endocardial mapping device and the physiological data is electrophysiological data.

31. The method as recited in claim 30 in which the electrophysiological data produced by the endocardial mapping device is displayed as an electrical activation map that overlays the registered image displayed in step iii).

32. The method as recited in claim 28 in which the medical procedure includes the use of an ablation device and the location of the ablation device with respect to the subject is depicted in the images acquired in step d).

33. The method as recited in claim 32 in which a depiction of the ablation device overlays the registered image displayed in step iii).

34. A method for performing a medical procedure using a medical device on a subject which moves in a repetitive functional cycle, the steps comprising:

a) acquiring image data of the subject during successive phases of the functional cycle prior to performing the medical procedure;

b) reconstructing a model image of the subject which depicts the subject at successive phases of the functional cycle;

c) storing the model image;

d) acquiring information as the medical procedure is being performed which indicates the location of the medical device relative to the subject;

e) detecting the phase in the functional cycle of the subject as the medical procedure is being performed; and f) producing images as the medical procedure is being performed by:
   i) selecting from the stored model image an image which depicts the subject at the currently detected functional cycle phase;
   ii) registering the medical device with the image selected in step i) using the information currently acquired in step d);
   iii) displaying an image depicting information related to the registered medical device; and
   iv) repeating steps i), ii), and iii).

35. The method as recited in claim 34 which includes acquiring physiological data from the subject with the medical device during the medical procedure and the depicted information is derived from the acquired physiological data.

36. The method as recited in claim 35 in which the medical device is an endocardial mapping device and the physiological data is electrophysiological data.

37. The method as recited in claim 36 in which the electrophysiological data produced by the endocardial mapping device is displayed as an electrical activation map that overlays the image displayed in step iii).

38. The method as recited in claim 37 in which the medical procedure includes the use of an ablation device and the location of the ablation device is also acquired in step d) with respect to the subject and the ablation device is also depicted in the image produced in step iii).

39. The method as recited in claim 34 in which the medical procedure includes the use of an ablation device and the location of the ablation device is acquired in step d) with respect to the subject and the ablation device is depicted in the image produced in step iii).

* * * * *